(12) United States Patent
Ostafin et al.

(10) Patent No.: US 10,675,641 B2
(45) Date of Patent: *Jun. 9, 2020

(54) METHOD AND APPARATUS FOR CONTINUOUS REMOVAL OF SUB-MICRON SIZED PARTICLES IN A CLOSED LOOP LIQUID FLOW SYSTEM

(71) Applicant: Nanoshell Company, LLC, North Salt Lake, UT (US)

(72) Inventors: Agnes Ostafin, North Salt Lake, UT (US); Hiroshi Mizukami, Pasadena, CA (US)

(73) Assignee: Nanoshell Company, LLC, North Salt Lake, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/160,873

(22) Filed: Oct. 15, 2018

(65) Prior Publication Data

US 2019/0151861 A1    May 23, 2019

Related U.S. Application Data

(63) Continuation of application No. 15/351,157, filed on Nov. 14, 2016, now Pat. No. 10,099,227, which is a
(Continued)

(51) Int. Cl.
*B04B 7/08* (2006.01)
*B04B 11/02* (2006.01)
(Continued)

(52) U.S. Cl.
CPC .............. *B04B 7/08* (2013.01); *A61M 1/3679* (2013.01); *A61M 1/3687* (2013.01);
(Continued)

(58) Field of Classification Search
CPC .............. A61M 1/3679; A61M 1/3687; A61M 1/3693; A61M 1/3696; B01D 21/262;
(Continued)

(56) References Cited

U.S. PATENT DOCUMENTS

| 4,387,848 A | 6/1983 | Kellogg et al. |
| 4,479,790 A | 10/1984 | Bocckino et al. |

(Continued)

FOREIGN PATENT DOCUMENTS

| CA | 1298822 | 4/1992 |
| CN | 101172207 | 5/2008 |

(Continued)

OTHER PUBLICATIONS

Andres, Christine, et al., "Anisotropic Calcium Phosphate Nanoparticles Coated with 2-Carboxyethylphosphonic Acid", J. Mater. Chem. vol. 16, 2006, 3964-3968.

(Continued)

*Primary Examiner* — Timothy C Cleveland
(74) *Attorney, Agent, or Firm* — Peacock Law P.C.; Janeen Vilven

(57) ABSTRACT

A centrifuge rotor having a curved shape is offset on a spinning rotor base and creates contiguous areas of low to high centrifugal force depending on the distances from the axis of the rotor base and a method of separating components in a fluid based upon a difference in density of the components, the method comprising the steps of providing to a rotor as described herein the fluid containing the mixed together components to be separated based upon the difference in density of the mixed together components; continuously flowing the components in the fluid to the rotor through an input tube connected to the input port while the rotor is spinning about a centrifugal axis of rotation; separating the components in the fluid into fractions based upon
(Continued)

the difference in density of the mixed together components with the use of centrifugal force when the rotor is spinning; collecting components having i) a first density via a first tube connected to the output port at the first end on the rotor, ii) a second density via a second tube connected to the output port at the second end on the rotor, iii) a third density via a third tube connected to the output port at the junction on the rotor and iv) a fourth density via a fourth tube connected to the output port between the input port and the output port at the first end.

20 Claims, 3 Drawing Sheets

Related U.S. Application Data continuation-in-part of application No. 14/803,361, filed on Jul. 20, 2015, now Pat. No. 9,956,180, which is a continuation-in-part of application No. 13/322,790, filed as application No. PCT/US2010/046421 on Aug. 24, 2010, now abandoned.

(60) Provisional application No. 61/236,810, filed on Aug. 25, 2009.

(51) Int. Cl.
| | | |
|---|---|---|
| C12M 1/00 | (2006.01) | |
| C12M 1/26 | (2006.01) | |
| A61M 1/36 | (2006.01) | |
| B01D 21/26 | (2006.01) | |
| B01D 21/34 | (2006.01) | |
| B04B 5/04 | (2006.01) | |
| B04B 13/00 | (2006.01) | |

(52) U.S. Cl.
CPC ........ *A61M 1/3693* (2013.01); *A61M 1/3696* (2014.02); *B01D 21/262* (2013.01); *B01D 21/34* (2013.01); *B04B 5/0442* (2013.01); *B04B 11/02* (2013.01); *B04B 13/00* (2013.01); *C12M 33/10* (2013.01); *C12M 47/04* (2013.01); *B04B 2005/045* (2013.01); *B04B 2013/006* (2013.01)

(58) Field of Classification Search
CPC ........ B01D 21/34; B04B 5/0442; B04B 7/08; B04B 13/00; B04B 2005/045; B04B 2013/006
See application file for complete search history.

(56) References Cited

U.S. PATENT DOCUMENTS

| | | |
|---|---|---|
| 5,123,901 A | 6/1992 | Carew |
| 5,386,734 A | 2/1995 | Pusinelli |
| 5,635,207 A | 6/1997 | Grinstaff et al. |
| 5,641,622 A | 6/1997 | Lake et al. |
| 5,663,051 A | 9/1997 | Vlasselaer |
| 5,679,394 A | 10/1997 | Long, Jr. et al. |
| 5,811,521 A | 9/1998 | Kluger et al. |
| 5,840,502 A | 11/1998 | Van Vlasselaer |
| 6,071,422 A | 6/2000 | Hlavinka et al. |
| 6,277,060 B1 | 8/2001 | Neumann |
| 6,280,375 B1 | 8/2001 | Meisberger et al. |
| 6,416,456 B2 | 7/2002 | Zanella et al. |
| 6,497,674 B1 | 12/2002 | Steele et al. |
| 7,297,272 B2 | 11/2007 | Min et al. |
| 7,531,133 B2 | 5/2009 | Hole |
| 8,449,489 B2 | 5/2013 | Thorn et al. |
| 9,415,021 B2 | 8/2016 | Ostafin |
| 9,956,180 B2 | 5/2018 | Ostafin et al. |
| 10,099,227 B2 | 10/2018 | Ostafin et al. |
| 2003/0026024 A1 | 2/2003 | Igarashi |
| 2003/0026855 A1 | 2/2003 | Kameneva et al. |
| 2003/0036518 A1 | 2/2003 | Samain et al. |
| 2004/0102732 A1 | 5/2004 | Naghavi et al. |
| 2005/0087122 A1 | 4/2005 | Ismagilov et al. |
| 2006/0003439 A1 | 1/2006 | Ismagilov et al. |
| 2006/0240964 A1 | 10/2006 | Lolachi et al. |
| 2006/0280798 A1 | 12/2006 | Ensoli |
| 2007/0026024 A1 | 2/2007 | Drees |
| 2007/0258888 A1 | 11/2007 | Feldmann |
| 2009/0088679 A1 | 4/2009 | Wood et al. |
| 2011/0105982 A1 | 5/2011 | Leonard et al. |
| 2011/0201986 A1 | 8/2011 | Howell et al. |
| 2011/0224645 A1 | 9/2011 | Winqvist et al. |
| 2012/0077662 A1 | 3/2012 | Ostafin et al. |
| 2012/0164231 A1 | 6/2012 | Ostafin et al. |
| 2014/0008301 A1 | 1/2014 | Ostafin et al. |
| 2014/0175018 A1 | 6/2014 | Winqvist et al. |
| 2015/0238432 A1 | 8/2015 | Ostafin et al. |
| 2015/0321204 A1 | 11/2015 | Ostafin et al. |
| 2016/0038668 A1 | 2/2016 | Ostafin et al. |
| 2017/0056891 A1 | 3/2017 | Ostafin et al. |

FOREIGN PATENT DOCUMENTS

| | | |
|---|---|---|
| CN | 101322029 | 12/2008 |
| EP | 0416575 | 3/1991 |
| WO | 1995/028915 | 11/1995 |
| WO | 1999/002269 | 1/1999 |
| WO | 2005/097208 | 10/2005 |
| WO | 2006/020100 | 2/2006 |
| WO | 2006/115938 | 11/2006 |
| WO | 2008/107167 | 9/2008 |
| WO | 2011/025755 | 3/2011 |
| WO | 2011/025756 | 3/2011 |
| WO | 2014/008490 | 1/2014 |

OTHER PUBLICATIONS

Baran, J., et al., "Detection of Cancer Cells in the Blood by FACS Sorting of CD45-Cells", Int. J. Mol. Med., vol. 1, No. 3, 1998, 573-581.

Beltinger, C. P., et al., "A Simple Combined Microdissection and Aspiration Device for the Rapid Procurement of Single Cells from Clinical Peripheral Blood Smears", Mol. Path., vol. 51, No. 4, 1998, 233-236.

Brandt, Burkhard, et al., "Two-Layer Buoyant Density Centrifugation Gradient for Enrichment of Prostate-Derived Cells and Cell Clusters from Peripheral Blood", Clinical Chemistry, vol. 42, No. 11, 1996, 1881-1882.

Brugger, Wolfram, et al., "Mobilization of Tumor Cells and Hematopoietic Progenitor Cells Into Peripheral Blook of Patients With Solid Tumors", Blood, vol. 83, No. 3, 1994, 636-640.

Buckner, Dean, et al., "Leukapheresis by Continuous Flow Centrifugation (CFC) in Patients with Chronic Myelocytic Leukemia (CML)", Blood, vol. 33, 1969, 353-369.

Campana, D., et al., "Detection of Minimal Residual Disease in Acute Leukemia: Methodologic Advances and Clinical Significance", Blood, vol. 85, No. 6, 1995, 1416-1434.

Chang, Thomas Ming Swi, "Blood Substitutes Based on Nanobiotechnology", Trends in Biotechnology, vol. 24, No. 8, 2006, 372-377.

Denis, Marc G., et al., "Detection of Disseminated Tumor Cells in Peripheral Blood of Colorectal Cancer Patients", Int J Cancer, vol. 74, No. 5, 1998, 540-544.

Glaves, D., et al., "Haematogenous Dissemination of Cells from Human Renal Adenocarcinomas", Br J Cancer, vol. 57, 1988, 32-35.

Harlozinska, Antonina, et al., "Density Distribution, Cytomorphologic Features and Immunologic Characteristics of Ovarian and Endometrial Clear Cell Carcinomas", Acta Cytologica, vol. 34, No. 5, 1990, 657-663.

Henkel-Hanke, Thad, et al., "Artificial Oxygen Carriers: A Current Review", AANA Journal, vol. 75, No. 3, 2007, 205-211.

(56) References Cited

OTHER PUBLICATIONS

Hester, Jeane P., et al., "Principles of Blood Separation and Component Extraction in a Disposable Continuous-Flow Single-Stage Channel", Blood, vol. 54, No. 1, 1979, 254-268.

Hill, S. E., "Oxygen Therapeutics—Current Concepts", Canadian Journal of Anaesthesia, vol. 48, No. 4, 2001, S32-S40.

Jahr, J. S., "Blood Substitutes as Pharmacotherapies in Clinical Practice", Curr Opin Anaesthesiology, vol. 20, No. 4, 2007, 325-330.

Judson, George, et al., "Closed Continuous-Flow Centrifuge", Nature vol. 217, 1968, 816-818.

Kabalnov, Alexey, et al., "Phospholipids as Emulsion Stabilizers. 1. Interfacial Tensions", Langmuir, vol. 11, No. 8, 1995, 2966-2974.

Karczewski, Donna M., et al., "The Efficiency of an Autotransfusion System for Tumor Cell Removal from Blood Salvaded During Cancer Surgery", Anesth Analg, vol. 78, No. 6, 1994, 1131-1135.

Keipert, Peter E., "OxygentTM, a Perfluorochemical-Based Oxygen Therapeutic for Surgical Patients", Blood Substitutes, Chapter 28, 2006, 312-323.

Kim, H. W., et al., "Artificial Oxygen Carriers as Red Blood Cell Substitutes: a Selected Review and Current Status", Artificial Organs, vol. 28, No. 9, 2004, 813-828.

Klein, Jan, et al., "Transperitoneal Oxygenation with Fluorocarbons", Anesthesia and Analgesia, vol. 65, No. 7, 1986, 734-738.

Koch, Colleen Gorman, et al., "Duration of Red-Cell Storage and Complications after Cardiac Surgery", N Engl J Med, vol. 358, 2008, 1229-1239.

Ness, Paul, "Oxygen Therapeutics-Pursuit of an Alternative to the Donor Red Blood Cell", Arch Pathol Lab Med, vol. 131, No. 5, 2007, 734-741.

Ng, Cheng E., et al., "Buoyant Density of EMT6 Fibrosarcoma Cells", Cell Biophysics, vol. 2, No. 2, 1980, 153-163.

Racila, Emilian, et al., "Detection and Characterization of Carcinoma Cells in the Blood", Proc Natl Acad Sci, vol. 95, No. 8, 1998, 4589-4594.

Sabile, A., "Efficiency of Ber-EP4 Antibody for Isolating Circulating Epithelial Tumor Cells Before TR-PCR Detection", Am J Clin Pathol, vol. 112, No. 2, 1999, 171-178.

Schmidt, Hartley Tyler, "Calcium Phosphate Based Nanoshell for use in Biomedical Applications", University of Notre Dame Electronic Theses & Disertations, 2006, 1-347.

Suarez-Quian, C. A., "Laser Capture Microdissection of Single Cells from Complex Tissues", Biotechniques, vol. 26, No. 2, 1999, 328-335.

Thomas, Terry E., et al., "Purification of Hematopoietic Stem Cells for Further Biological Study", Methods, vol. 17, No. 3, 1999, 202-218.

METHOD AND APPARATUS FOR CONTINUOUS REMOVAL OF SUB-MICRON SIZED PARTICLES IN A CLOSED LOOP LIQUID FLOW SYSTEM

CROSS REFERENCE TO RELATED APPLICATIONS

This application is a continuation of U.S. patent application Ser. No. 15/351,157 entitled "Method and Apparatus for Continuous Removal of Sub-Micron Sized Particles in a Closed Loop Liquid Flow System", filed on Nov. 14, 2016, which is a Continuation-in-Part of U.S. patent application Ser. No. 14/803,361 entitled "Method and Apparatus for Continuous Removal of Submicron Sized Particles in a Closed Loop Liquid Flow System", filed on Jul. 20, 2015, and issued on May 1, 2018 as U.S. Pat. No. 9,956,180, which is a Continuation-in-Part of U.S. patent application Ser. No. 13/322,790, entitled "Method and Apparatus for Continuous Removal of Submicron Sized Particles in a Closed Loop Liquid Flow System", filed on Nov. 28, 2011, and now abandoned, which is a National Stage Entry of International Patent Application PCT/US10/46421, entitled "Method and Apparatus for Continuous Removal of Submicron Sized Particles in a Closed Loop Liquid Flow System, filed on Aug. 24, 2010, which claims priority to and the benefit of U.S. Provisional Patent Application Ser. No. 61/236,810, entitled "Synthesis of Oxygen Carrying, Turbulence Resistant High Density Submicron Particulates and Method for Their Continuous Retrieval from the Blood Including Submicron Size Perfluorocarbon Emulsion and PolyHb Dual-Cored Oxygen Carries (DCOC)", filed on Aug. 25, 2009. The specification and claims thereof are incorporated herein by reference

BACKGROUND OF THE INVENTION

Field of the Invention

The present invention relates to a method and apparatus for continuous removal of sub-micron sized particles from the blood or other liquids. In many different fields, liquids carrying particles are processed to separate the liquid from the particles and/or to obtain either a purified liquid or purified particle end product. Whole blood consists of various liquid components and particle components. The liquid portion of blood is largely made up of plasma, and the particle components include red blood cells (erythrocytes), white blood cells (leukocytes), and platelets (thrombocytes). While these constituents have similar densities, their average density relationship, in order of decreasing density, is as follows: red blood cells, white blood cells, platelets, and plasma. In addition, the particle components are related according to size, in order of decreasing size, as follows: white blood cells, red blood cells, and platelets. Most current purification devices rely on density and size differences or surface chemistry characteristics to separate and/or filter the blood components.

One method of separating the components in blood from each other is to centrifuge the blood. Centrifugal separation of components in solution depends on the difference of density between the solutes and solvent. Under the centrifugal field, if the density of a solute is higher than that of the solvent, then the solute will move in the direction of the centrifugal field strength until they become equal. Under the velocity centrifugation, the velocity of the solute as the solute moves in the field of centrifugation is the concern. In the equilibrium centrifugation the motion of the solute will stop as its density becomes equal to the field of density gradient created in the device.

In an aphaeresis centrifuge, a small density gradient is self generated by the centrifugation of blood and each blood component separates to within a density gradient that correlates to the density of the component. As the components are released steadily through the outlet ports of the centrifuge rotor, the overall density gradient within the rotor will remain nearly the same during the centrifugation as untreated blood enters the rotor at about the flow rate that equals the exit flow rate.

The human blood consists of wide ranges of nucleated and enucleated cells, high density extracellular vesicles (EVs), molecules, ions and water. In the healthy body, the levels of all these components are regulated and kept at within the acceptable levels. Their deviation from the normal range is a sign of disease indicating that a patient could benefit for treatment such as drugs, radiation, surgery etc. Reducing the levels of these compounds in the blood physically may contribute to the treatment of the disease. Removal of invasive toxins from the circulation would also improve the patient's health.

SUMMARY OF THE INVENTION

One embodiment of the present invention provides for a rotor for a centrifuge used to separate a mixture of components in a fluid having different densities. The rotor comprises a hollow curved housing that has an inner wall and an outer wall, a top, a bottom and a first end and a second end wherein the inner wall is radially closer to an axis of rotation as compared to the outer wall. The hollow curved housing being formed of a curved first rotor element that terminates at the first end of the curved housing and a curved second rotor element that terminates at the second end of the curved housing wherein the curved housing between the curved first rotor element and the curved second rotor element includes a step down junction that steps down from the first rotor element to the second rotor element and makes the first rotor element continuous with the second rotor element. The curved housing may form for example a curve that is between 150-360 degrees. On the inner wall of the first rotor element is an input port that is positioned between an output port of the first end and an output port positioned on the inner wall of the junction. An output port is positioned on the inner wall of the first rotor element between the output port at the first end and the input port. The second end includes an output port. The position of the input port, the output port at the first end, and the output port at the second end can be positioned in the same horizontal plane of the rotor. Each port can be connectable to a tube. The hollow curved housing from the first end to the second end forming an about 150-200 degree curve about the axis of rotation. The first end is a distance $d4$ from the axis of rotation, the second end is a distance $d3$ from the axis of rotation and the junction is a distance $dr$ from the axis of rotation with $d4>dr>d3$.

In one embodiment, the output port positioned on the inner wall of the junction is positioned at the center of the junction.

In one embodiment, the hollow housing has a distance between an interior side of the inner wall and an interior side of the outer wall that is the same in the first rotor element and the second rotor element.

In one embodiment the area defined by the first rotor element between $d4$ and $dr$ is greater than the area defined by the second rotor element between $dr$ and $d3$.

In one embodiment the junction between the first rotor element and the second rotor element is not angled.

Another embodiment of the present invention provides a method of separating components in a fluid based upon a difference in density of the components in the fluid when the components mixed together have at least four different densities, the method comprising the steps of providing to a rotor according to one embodiment of the present invention the fluid containing the mixed together components to be separated based upon the difference in density of the mixed together components. Continuously flowing the components in the fluid to the rotor through an input tube connected to the input port while the rotor is spinning about a centrifugal axis of rotation. The components in the fluid are separated into fractions based upon the difference in density of the mixed together components with the use of centrifugal force when the rotor is spinning. Components having i) a first density via a first tube connected to the output port at the first end on the rotor, ii) a second density via a second tube connected to the output port at the second end on the rotor, iii) a third density via a third tube connected to the output port at the junction on the rotor and iv) a fourth density via a fourth tube connected to the output port between the input port and the output port at the first end are collected. The components having a first density may comprise high density sub-micron particles that have a density greater than the components with a second density, a third density or a fourth density. For example the high density sub-micron particles are functionalized to capture a first component from the components mixed together in the fluid. The fluid may be supplied to the rotor via the input tube by a pump such as a peristaltic pump. The fluid collected from a first tube, a second tube, or a fourth tube are pumped from the rotor to a reservoir. The reservoir can be an animal such as a human or a container.

In one embodiment the fluid is blood and the components having a first density includes exosomes or oncosomes, the components having a second density include plasma, the components having a third density includes buffy coat with or without circulating tumor cells and the components having a fourth density include red blood cells.

Another aspect of the present invention provides a rotor as described herein for a centrifuge used to separate natural whole blood from artificial blood having a density higher than any of the components of the natural whole blood.

In another embodiment a method of separating components in a fluid during centrifugation is based upon a difference in density of the components in the fluid. The method includes the steps of providing to a rotor as described herein a fluid containing the mixed together components to be separated and continuously flowing the fluid having the components to the rotor while the rotor is spinning at high speed (for example, 2400 rpm). The components in the fluid are separated based upon the difference in density with the use of centrifugal force when the rotor is spinning. The components having a first density are collected via a first tube located at a first position on the rotor and the components having a second density are collected via a second tube located at a second position on the rotor and the components having a third density are collected via a third tube at a third position on the rotor. The components having a first density comprise high density particles for example particles that are natural or artificial (for example exosomes or oncosomes including large oncosomes that have a density different than the components with a second density or components with a third density and wherein the high density particles can be functionalized to capture a first component from the components mixed together in the fluid.

Embodiments of the present invention provides a system and method to specifically remove unwanted materials (targets) from the blood by treating the blood within a rotor as disclosed herein to centrifugal forces and removing the targets from the rotor during density sensitive centrifugation. Similarly, some unwanted high density EVs in the blood can also be removed from the blood with the rotor and centrifuge system and method as disclosed herein. An embodiment of a rotor as disclosed herein is also capable of removing specific targets from other liquids and solvents before or after the targets have been attached to a high density sub-micron particle functionalized to bind to the specific target.

A high density sub-micron particle as referenced herein may have intrinsic biological function, such as use as a perfluorocabon based artificial oxygen carrier (AOC). The AOC may have to be centrifugally collected from the blood and removed, by taking advantage of their density being higher than that of the blood components. An AOC can be injected into the blood of a patient and when no longer needed it is removed for example with the system and method as disclosed herein The benefits of other types of high density sub-micron particles may be found in their ability to capture the desired targets after the sub-micron high density particles are functionalized to conjugate with the specific cells, molecules and ions in the blood. Similarly, the functionalized sub-micron high density particles may be able to capture circulating tumor cells (CTC), sickle cell hemoglobin (HbS), toxins, irons etc. in the blood and then be retrieved from the blood as the blood containing the functionalized high density sub-micron particles with and without the target attached thereto are removed from the blood extra-corporeally using an embodiment of the centrifuge rotor described herein.

The densities of some of the EVs, i.e. oncosomes, large oncosomes and other cancer related microvesicles are higher than 1.12 g/ml and can be isolated with an embodiment of a method as disclosed herein.

In one embodiment of the present invention, the densities of sub-micron particles of interest are 1.12 g/ml or higher and are significantly higher than those of the highest density components found in blood, namely 1.11 g/ml of red blood cell (RBC), and mostly synthetic organic and polymeric materials. Separating materials with such large differences in density is possible with a rotor as described herein as compared to those described for use in conventional clinical aphaeresis instruments.

An embodiment of a rotor as described herein will continuously or intermittently isolate a target having a density that is different as compared the density of other elements in the liquid, i.e. blood components (for example whole blood or a subfraction thereof). The isolation of the target can be achieved continuously and quickly for example during the time it takes for a volume of blood to enter the rotor system and return to the subject being treated. The circulation time of a given volume of liquid through the system depends on the pump flow rate. In this embodiment, since the separation is continuous, there is no limit to the volume of liquid to be treated. In one embodiment of the rotor, the reservoir within the rotor can hold a volume of liquid to be treated. The volume of liquid in the rotor is about 15 mls and the volume of liquid in the tubes leading to and from the rotor during the treatment process will be about 20 mls. This will be close to 1 min of pumping rate. Thus, the volume of exo-corporeal blood flowing from a patient being treated to the system during treatment can be made to about 35-40 mls/min with the treated blood flowing back to the patient.

In another embodiment the rotor can be used to continuously or intermittently to isolate high density targets including sub-micron particles such as exosomes, oncosomes and rNP from other biological fluids, cell lysates, macromolecule or polymer solutions etc.

DESCRIPTION OF THE DRAWINGS

The invention will be better understood upon reading the following Detailed Description in conjunction with the drawings in which.

DETAILED DESCRIPTION

Figure 1:
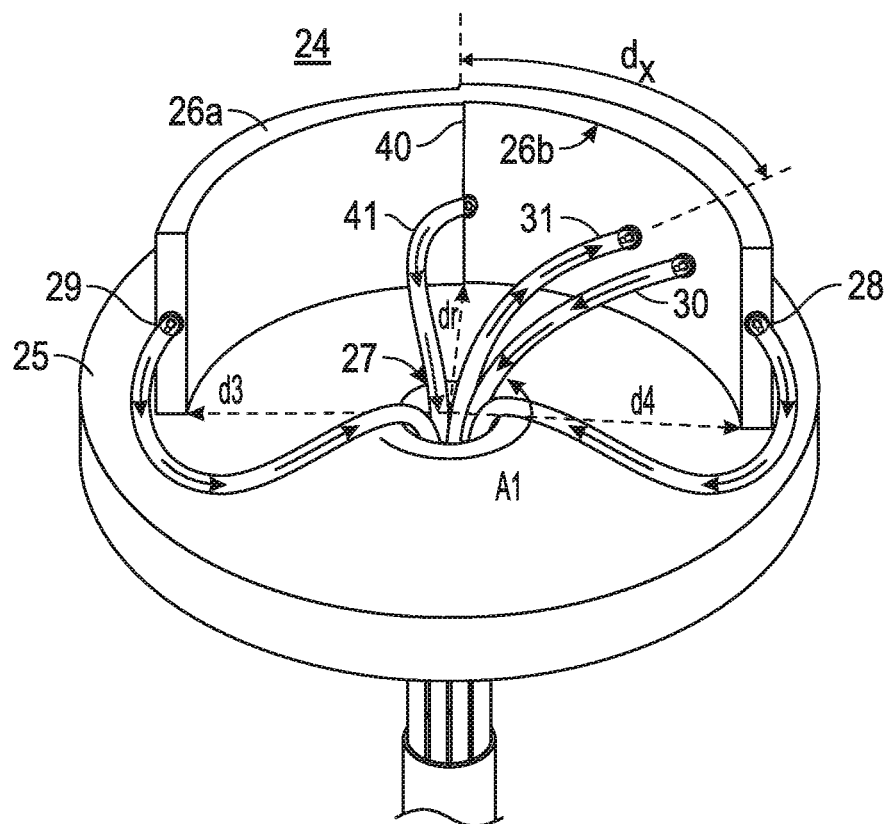
FIG. 1 is a perspective view of the novel centrifuge that utilizes density gradient separation to efficiently remove particulate artificial oxygen carriers from blood or other biofluids.

As used herein "a", "an" and "the" means one or more unless otherwise specified.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ±a range of up to 20%, up to 15%, up to 10%, up to 5%, or up to 4%, 3%, 2%, or 1% compared to the specifically recited value.

The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the invention necessarily includes the listed ingredients, and is open to unlisted ingredients that do not materially affect the basic and novel properties of the invention. A "consisting essentially of" claim occupies a middle ground between closed claims that are written in a closed "consisting of" format and fully open claims that are drafted in a "comprising' format". These terms can be used interchangeably herein if, and when, this may become necessary. Furthermore, the use of the term "including", as well as other related forms, such as "includes" and "included", is not limiting.

As used herein "density" is considered to include a specified density and/or a desired density range close to the specified density for components that separate to different regions of the rotor based upon the density of the fluid in which the components are carried, the rotation speed of the rotor and the flow rate of the fluid to and or from a rotor as described herein.

"Extracellular vesicles (EVs)" are general expressions for enucleated vesicles from the normal and diseased cells. Exosomes are cell-derived vesicles of 30-100 nm in diameter and oncosomes are cancerous cell origin. Large oncosome could be as large as 1 μm.

During the continuous flow of liquid to a rotor as described herein, the spinning rotor is designed to separate the components of the liquid according to the densities of components located within the liquid and to collect the components of highest, lowest and other defined densities via tubes connected to separate openings/ports in the rotor. The components separate in a density gradient. The blood or other fluid or solution having components to be separated based upon a difference in density will enter the centrifuge rotor through a port and the components will be separated to high density on one end of the rotor and low density on the other end. Components with densities between the two limits will concentrate at a position between the two ends for example near in the middle of the rotor. The different density fractions to be collected will leave the rotor through separate ports. The entering flow rate of blood or other fluid solution will often be determined by an external requirement such as the status of a patient and the desired purity of separation for each fraction. The flow rate can be adjusted by a dedicated pump. In one embodiment to adjust the exit flow rates through one or more exit ports multiple pumps are used. For example two pumps are used when there are two, three or four or more exit ports. In a preferred embodiment there is a flow rate assigned to each outlet port which can be the same or independently selected for each outlet port which can be controlled by one or more pumps. The rate of each outward flow rate will be defined by the type of component to be captured at each exit port and the high-density component (for example, exosome and oncosomes) to be captured, and the source fluid carrying both.

In one embodiment, the system and method is designed to treat a patient's blood when the blood is flowing from the patient to the device and to return the blood to the patient in real time. The rate of flow of the blood entering the rotor should be compatible with the rates of blood flows in the blood vessels of the subject, around 32 ml/min. Thus, total flow rate from the patient return output ports should be about 32 ml/min according to one embodiment of the present invention. In one embodiment, the flow rate through each tube carrying fluid to and away from the rotor will be limited by mechanism employed to ensure that the input tube and output tube(s) remain kink-free as the rotor spins (several methods are currently used in aphaeresis systems and are known in the art).

The rotor and method as described according to one embodiment of the present invention distinguishes itself from other clinical aphaeresis rotors by collecting the desired naturally occurring components of blood in a single flow path, separate from materials with buoyant densities higher than 1.2 g/ml. Examples of cells, molecules, and ions that can be continuously retrieved with the proposed centrifugal device from the circulating blood include circulating tumor cells, ABO type red blood cells, macrophages, sickle cell hemoglobin, AOC, antigens, antibodies, drugs, toxins, and irons but are not limited thereto.

A rotor according to one embodiment of the present invention would be able to separate continuously any particles in the flowing liquid through the rotor according to their densities when the system is exerting centrifugal force on the liquid.

FIG. 1 illustrates a front view of a rotor according to one embodiment of the present invention. To make the drawing simpler so the invention can be better understood, the case of the centrifuge rotor is not shown in FIG. 1. Rotor 24 is positioned on a circular rotor base 25 that is mounted on an axis 27 to a motor driven shaft. As shown in FIG. 1, the rotor base 25 is rotated in a counter clockwise direction for the rotor 24 configuration shown and described herein. It should be understood that the rotor can be rotated in a clockwise direction with similar results. The blood having mixed components (such as one or more of the following: CTC, RBC, rNP, exosome, oncosome, water, plasma) enter into the rotor at port 31 located on the inner wall of a first rotor element 26b. The area bordered by rotor element 26b and the lines d4 and dr is greater than the area bordered by rotor element 26a, and the lines dr and d3. As the base 25 rotates about the center of axis 27 a density based gradient of blood is created by the centrifugal field on the rotor and components therein. The light density plasma exits at output port 29 on a second end of the rotor and the higher density components such as oncosomes and exosomes exit from output port 28 on a first end of the rotor, while circulating tumor cells (CTC) located within the buffy coat density fraction exit from output port 41 near the junction 40 and red blood cells exit from output port 30 located between output port 28 and output port 41. From port 41, platelets and white cells exit. If high density retrievable nanoparticels, (rNP) are mixed in the blood, they would exit from port 28 when the rNP density is engineered to be a desired density that is higher than those of a red blood cell. In addition, if there are extracellular vesicles (EVs), such as exosomes, oncosomes, large oncosomes etc, these components would also exit from port 28 through tube 28. Port 28 at the first end and port 29 at the second end are in fluid communication with each other. Using this apparatus, exosomes or oncosome could be extracted from the other blood components of a subject suspected of having cancer or a patient being treated for cancer, for example. The oncosomes and exosomes would be separated from a circulating tumor cell (CTC), which is collected at tube 41 after the CTC exits port 41 of the rotor. Removing oncosomes and large oncosomes from the blood of cancer patients would contribute for their treatment, diagnosing the nature of cancer, as well as a change in their levels in the blood may be used as a measure of effectiveness of treatments or recovery of the patients from the disease. In one embodiment the degree of curve is greater in the first rotor element 26b as compared to the degree of curve in the second rotor element 26a. In an alternative embodiment the degree of curve is greater in second rotor element 26a as compared to the degree of curve in the first rotor element 26b. In yet another embodiment the curve of 26b is equal to the curve of 26a.

Figure 2:
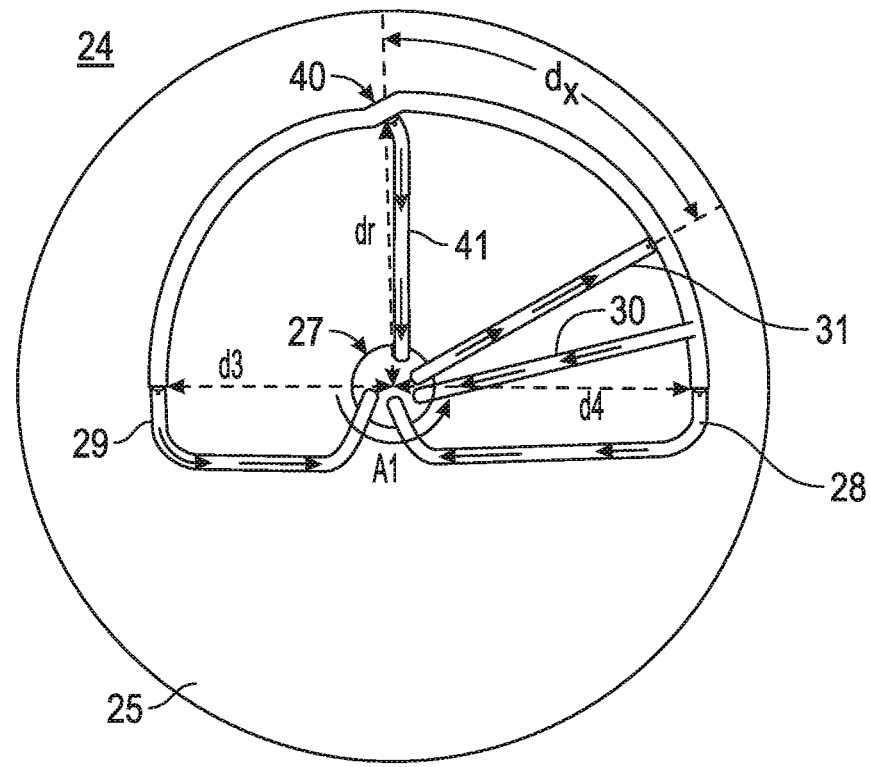
FIG. 2 is a top view of the novel centrifuge that better shows the novel rotor used in the centrifuge.
Figure 3:
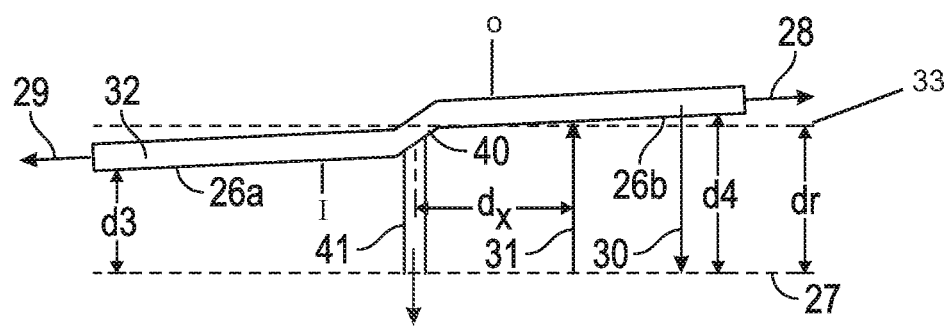
FIG. 3 is a linear graphical representation of the novel rotor of the centrifuge.

Distances d3, d4 and dr are shown in all of FIGS. 1, 2 and 3 to better understand how the rotor is positioned on the base 25. In one embodiment of the present invention distance d4>dr>d3. In one embodiment of the present invention the inner width of each rotor element 26a and 26b is about about 0.5 cm, the height is about 2 cm, and the length is about 15 cm. In one embodiment of the present invention, the reservoir volume of the rotor will be about 15 ml. However the exact measurements or dimensions of the rotor element can change as will be apparent to one of ordinary skill in the art. The fractionation or separation of the components based upon each components respective density within a fluid is continuous as the fluid flows through the system as the rotor is spinning. The dimensions of the rotor can be changed responding to the demand of the user, but the same principles of centrifugation apply.

Referring to FIG. 2, a top view of a rotor according to one embodiment of the present invention is illustrated. Rotor 24 is formed of two curved elements 26a and 26b which together form a curved hollow housing having a curve of between about 150-360 degrees or between about 150-200 degrees or between about 150-180 degrees or between about 180-200 degrees or about 180 degrees or less, or about 360 or 350 or 340 or 330 or 310 or 300 or 280 or 260 or 240 or 220 or 210 or 200 degrees or less around an axis of rotation. In one embodiment of the present invention the first end and the second end overlap. The first curved rotor element 26b extends from the arrow of d4 and ends at the arrow of dr. The second curved rotor element 26a extends from the arrow of d3 and ends at the arrow of dr. The distance from the axis of rotation 27 to any point along the inner wall of the first curved rotor element 26b is greater as compared to the distance from the axis of rotation 27 to any point along the inner wall of the second curved element 26a. The greater distance of first rotor element 26b from the axis of rotation creates a slightly higher centrifugal force on the components in the fluid within portion 26b of the rotor as compared to the components in the fluid within portion 26a of the rotor. The rotor is similar to that of a conventional aphaeresis instrument, but unlike the rotor of a conventional aphaeresis instrument, the rotor of FIG. 1 extends less than 360 degrees around an axis of rotation. The blood flow rate from the rotor to a receptacle (for example a patient (the donor or non-donor) or storage container) is as fast as 32 ml/min but can be faster or slower depending on the application. In one embodiment, the rotor can operate at 2400 rpm of spin speed to allow the density gradient to be quickly established and maintained, since the separation between the highest (1.2 g/ml) and the lowest (1.0 g/ml) density will be quickly established. However other spin speeds will be applied based upon the density of the fluid, the density of the components in the fluid and the separation of the components desired.

As seen in FIG. 3, even in the presence of a density as high as 1.9 g/ml, the fluid density gradient within the fluid will be quickly established and maintained. The density gradient difference between the components with the highest density and the lowest density is still about 0.9 g/ml, but it is spread over the entire length of the rotor. As seen in FIGS. 1, 2 and 3, the continuing curved elements help to separate the solutes according to their densities, while the solution is continuously being poured into the rotor at inlet port 31 and separated from each other based upon density continuously leaving from the other four ports under the centrifugal field strength. In one embodiment the length of the rotor is about 15 cm from a first end to a second end to permit subtle differences in density to be centrifugally separated with the rotor 24 when in use. In one example, the whole blood enters the rotor through input port 31 and the high density components such as RBC move towards output port 28 at the first end, while the low density components (such as plasma and white blood cells) move towards output port 41 and output port 29 at the second end. Thus adjusting the relative flow rates of the input and two output ports, it would be possible to adjust the profile of the component density gradient over the entire density gradient range of the rotor. In practice, the whole blood enters port 31 under the controlled flow rate by a pump (for example a peristaltic pump but is not limited thereto as other pumps are known to those skilled in the art). The flow rates of ports 28 and 29 can also be adjusted with one or more pumps and when multiple pumps are utilized, the net rates of all pumps define the out flow of blood from the port 30, but the density of the particles at port 30 will be defined by the ratio of these two pumps. Thus, adjusting the rpm of the centrifuge, pumping rates at 31, 28 and 29, it would be possible to what should be the density of particles, which come out from the port 30 at the known flow rate. In practice, however, the instrument will be usually adjusted so that only the high density retrievable particles and any attached materials should appear from port 28. With reference to FIG. 3, the inner wall ("I") is radially closer to an axis of rotation as compared to the outer wall ("O").

The different curvatures of rotor elements 26a and 26b and the offset of rotor element 26a, 26b on rotor base 25 relative to the centrifuge axis of rotation is illustrated in FIG. 2. When in use, rotor 24 is off centered on base 25 which itself is centered on the axis of rotation of the centrifuge resulting in regions of high, medium and low centrifugal force created on the rotor depending on the rotor distance from the axis of rotation 27. The distance dx is the distance from the center of junction 40 to input port 31. Tubing 30, 28, 29 and 41 carry components away from the rotor having a specified density range after the different density ranges are established in the rotor during centrifugation. Usually, the distance d3 is shorter than that of the distance d4.

FIG. 3 is a linear graphical representation of the novel centrifuge rotor 24 of the centrifuge to better illustrate the difference in distance from the axis of rotation for d4, dr and d3 relative to the input port and each output port. This figure shows how the distance between the face of composite rotor elements 26a, 26b and the stretched form of the axis of rotation 27 of centrifuge rotor 24 changes through the length of the rotor. Thus, the magnitude of centrifugal force at different regions of centrifuge rotor 24 are depicted by the distance from the axis of rotation 27, which is stretched and shown as the broken line at the bottom of FIG. 3. The distances d3, d4 and dr are shown in all of FIGS. 1, 2 and 3 to better understand how the figures relate to each other. Broken line 33 is a line that bisects junction 40 at its center and represents the hypothetical position of the center of the rotor if a perfect circle.

The relative distance between the axis of rotation line 27 and the position of each port reflects the centrifugal field strength, which is equivalent to the centrifugal force. As the centrifugal field strength is established within the aphaeresis rotor, the components will be separated, according to their densities, over the horizontally stretched out rotor elements 26a and 26b. Simply put, positions within the rotor element will be subject to different centrifugal field strengths generated by the centrifugal force and the components within the blood will fractionate according to their density along a density gradient corresponding to the field strength of the centrifugal force and collected through tubes connected with ports located in the rotor.

In one embodiment of the present invention, the whole blood obtained from a person who is connected in a closed loop system with a density gradient centrifuge as disclosed herein is input to the centrifuge rotor at input port 31. The whole blood is separated based upon the density of the components in the blood which permits separation of components within a density range at different locations in the rotor during centrifugation wherein components within a desired density are collected at different exit ports. The one or more separated components of the blood which flows from one or more exit ports can be returned to the person from whom the whole blood was withdrawn or stored in a container for later use or provided to another person. The component that is released from output port 28 or other output port can be collected and not returned. Exosomes and oncosome found in this fraction of the separated blood may indicate the disease state of the person. In one embodiment if any exosome or oncosomes are detected at exit port 41, a control circuit adjusts the flow rate of the blood via the adjustable pump(s) that permit the centrifuge rotor to fully separate any plasma from the exosomes and oncosome The centrifugal field generated in the density gradient centrifuge by centrifuge rotor 24 as it turns about the axis 27 (FIGS. 1 and 2) creates a density gradient field that changes between output ports 28 and 29. The result is that the lower density component fraction from whole blood is separated from the higher density component fraction from whole blood. In an alternative embodiment another output port may be added between output ports 28 and 29 such as between ports 41 and 30 or between ports 41 and 28 or between ports 41 and 29 or between ports 41 and 31 to separate intermediate density fractions of blood. The separated whole blood is withdrawn through the several output ports as previously described. The whole blood collected may be subjected to further fractionation. For example, further fractionation may be used to separate platelets and white blood cells from the whole blood in a manner known in the art.

With reference to FIG. 3, as the centrifugation begins the fluid of the input mixture entering the rotor at port 31 is separated based upon the density of the components with the highest density components being centrifugally forced closer to the outer wall ("O") of the rotor segment 26a and 26b. The components that have a density that is lower than the higher density components would fractionate in a density gradient with the least dense components being closer to the inner wall ("I") of the rotor segment 26b. The less dense component fraction moves laterally toward exit ports 41 and 29 with the least dense components exiting from port 29. The highest density components would exit from port 28 with those components having an intermediate density exiting from port 30 and 41. In FIGS. 1 and 2 the rotation is counter clockwise.

More particularly, as the blood continues to be injected into rotor at input 31 (shown in FIGS. 1-3), the blood components move towards the lower centrifugal field (direction of port 29) or move to the higher centrifugal field (direction of port 28) depending on the density of the blood components. The thickness of the curved housing of rotor 24 is about 5 mm according to one embodiment. The separation of the blood into components of different density is carried out very quickly and the blood will form layers based upon the density of the components in the blood. With separation being accomplished quickly it is possible to maintain the rate of blood inflow sufficiently fast to make the process "continuous-flow density separation". In one embodiment the curved rotor has a small offset (bend or protrusion) near the junction 40 of segments 26a and 26b to make the separation of the blood complete.

In one embodiment, near the exit port 28, there is output port 30, from which small samples are taken of the components flowing toward output port 28 to test the purity of the components exiting port 28. The purity of the components might change slowly over time during centrifugal retrieval of the components so the relative flow rates of pumps must be adjusted to maintain the purity of the components output at its port 28. Under a given revolution per minute of the rotor, to achieve the optimal removal of components from the blood, using the notation in FIG. 1, the following flow conditions must be met according to one embodiment of the present invention. $F31=F28+F29+F30+F41$ wherein F stands for flow rate. Each flow rate may be controlled by the corresponding monitor/pump. The liquid flow rate of the blood entering into the rotor through tube 31 will be set by the pump P31 at the desired flow rate.

According to one embodiment of the system and method of the present invention a rotor separates the components in the blood or fluid or solution according to their densities.

Figure 4:
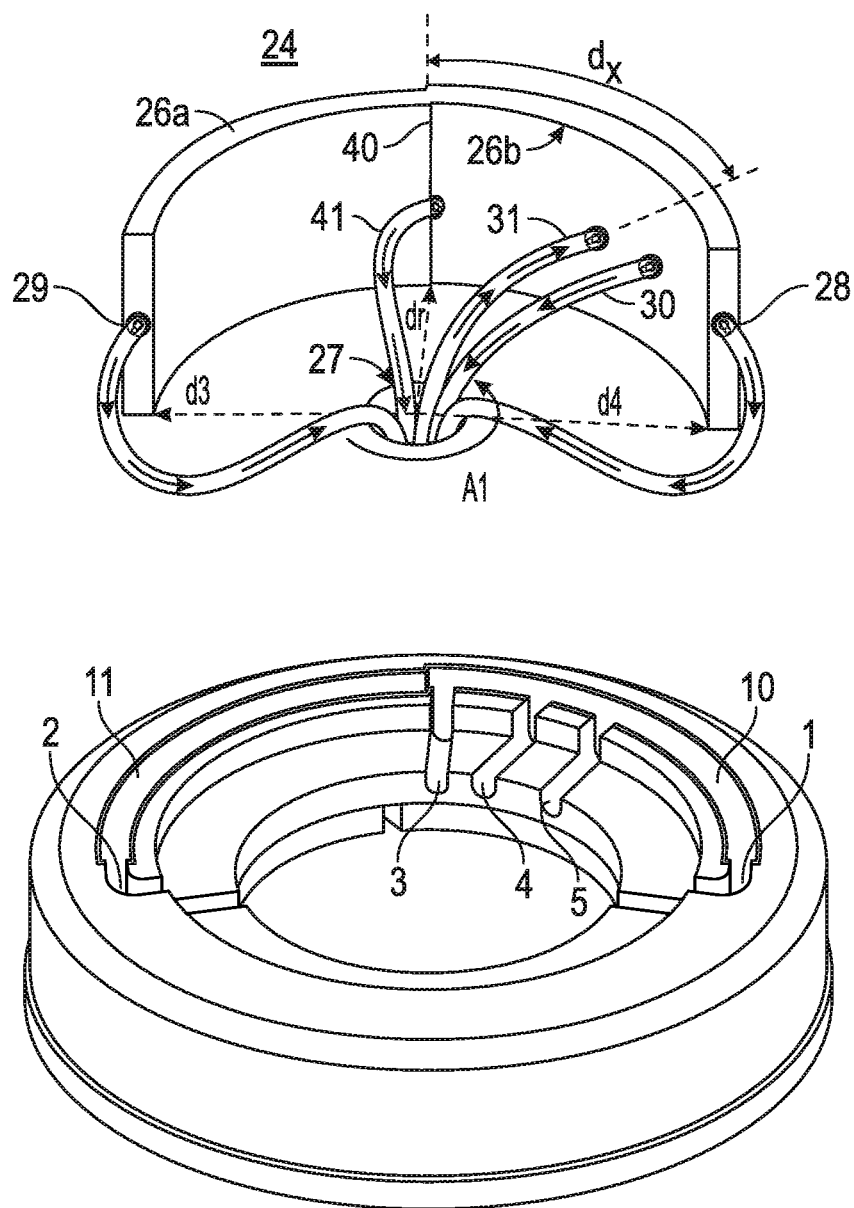
FIG. 4 illustrates a rotor and rotor housing according to one embodiment of the present invention.

The process of separation can occur during continuous flow of the liquid through the device. The rotor elements 26b and 26a are formed as a unitary housing. The rotor is removable positioned on the circular disc. The circular disc having a hole in the center to form a base of the rotor. FIG. 4 illustrates a rotor of FIG. 1 and a rotor base into which the rotor is positioned for use according to one embodiment of the present invention. The rotor base having grooves 10 and 11 to receive rotor elements 26b and 26a respectively. Groves 1, 2, 3, 4, and 5 are designed to accept tubes that are connected to output port 28, output 29, output port 41, input port 31 and output port 30 respectively. The tubes may follow a path through the center hole opening of the rotor base and are configured so that the base will be able to continuously spin, along with the rotor positioned thereon without the one or more tubes interfering with the rotation. One of the tubes is connected through a port located in the inner wall of side 26b and the blood or liquid will enter through port 31 by a pump. The rate of the flow is adjustable by the pump. The pump can be a peristaltic pump but is not limited thereto. The blood components that enter the rotor will be separated according to their densities with the highest density components exiting from the port 28 and the lowest density components exiting from port 29. The rates of outflows will be regulated with two separate pumps, one pump for each port. From port 29 the lowest density matter (plasma, water, and ions for example) will exit and from port 28 the highest density matter such as exosomes or oncosomes will exit. There is a third exit port 30 from which the components (for example red blood cells) with a density that is in between the higher density and lower density components will exit. The separation of the fluid (for example blood) will occur continuously with 100 ml or less of the fluid being in the rotor and tubes feeding the fluid to and from the rotor during the separation process as the fluid is being pumped from the source.

Various forms of aphaeresis instruments are currently in use to differentially collect blood components according to their densities. Most of the instruments are designed to accept red blood cells as the highest density components to collect. Even though the densities of microvesicles of blood are higher than those of RBC, they are significantly smaller in size and thus current aphaeresis instruments cannot be used to collect microvesicles. Assuming the out port 30 is the current maximum density for RBC, an additional port is needed to collect these high density, components but extremely small microvesicles of even less than 100 nm in diameter cannot be collected in one step. With a healthy subject, only exosomes will be collected from Port 28. But with cancer patients, exosomes, oncosomes and large oncosomes (if present) would be collected from Port 28, as their density ranges between 1.110 g/ml and 1.150 g/ml.

The novel density gradient separation technique taught and claimed herein may be used to separate other mixtures of substances having different densities. It may be used to separate and remove metastatic cancer cells from circulating blood. It may also be used for retrieval of low copy mammalian, bacterial or virus cells from blood. It may also be used to remove materials added to blood to enhance tissue and organ imaging. Depending on the application, the specific design requirement of these materials in terms of their size and composition may vary, but common to all of them are the properties summarized earlier, and the tailored ability for continuous retrieval from circulating fluids.

While what has been described herein is the preferred embodiment of the invention it will be understood by those skilled in the art that numerous changes may be made without departing from the spirit and scope of the invention. For example the rotor can be made rigid or flexible.

What is claimed is:

1. A rotor for a centrifuge used to separate a mixture of components in a fluid having different densities, the rotor comprising:
    a hollow curved housing that has an inner wall and an outer wall, a top, a bottom and a first end and a second end wherein the inner wall is radially closer to an axis of rotation as compared to the outer wall;
    the hollow curved housing being formed of a curved first rotor element that terminates at the first end of the curved housing and a curved second rotor element that terminates at the second end of the curved housing wherein the curved housing between the curved first rotor element and the curved second rotor element includes a junction that creates a change in an inner and outer radius of the first rotor element as compared to an inner and outer radius of the second rotor element;
    an input port positioned on the inner wall of the first rotor element between an output port of the first end and an output port positioned on the inner wall of the junction;
    an output port positioned on the inner wall of the first rotor element between the output port at the first end and the input port;
    an output port in the second end; and
    the hollow curved housing from the first end to the second end forming an about 150-360 degree curve about the axis of rotation;
    wherein the first end is a distance d4 from the axis of rotation, the second end is a distance d3 from the axis of rotation and the junction is a distance dr from the axis of rotation with d4>dr>d3.

2. The rotor of claim 1 wherein the output port positioned on the inner wall of the junction is positioned at the center of the junction.

3. The rotor element of claim 1 wherein the hollow housing has a distance between an interior side of the inner wall and an interior side of the outer wall that is the same in the first rotor element and the second rotor element.

4. The rotor element of claim 1 wherein the curve is between 180-200 degrees.

5. The rotor element of claim 1 wherein the input port, the output port at the first end, and the output port at the second end are each positioned in the same horizontal plane of the rotor.

6. The rotor element of claim 1 wherein the input port is connectable to a tube.

7. The rotor element of claim 1 wherein the area defined by the first rotor element between d4 and dr is greater than the area defined by the second rotor element between dr and d3.

8. The rotor element of claim 1 wherein the output port at the first end, the output port at the second end, the output port near the junction and the output port between the output port at the first end and the output port near the junction are each connectable to a tube.

9. A method of separating components in a fluid based upon a difference in density of the components in the fluid when the components mixed together have at least four different densities, the method comprising the steps of:
    providing to a rotor of claim 1 the fluid containing the mixed together components to be separated based upon the difference in density of the mixed together components;

continuously flowing the components in the fluid to the rotor through an input tube connected to the input port while the rotor is spinning about a centrifugal axis of rotation;

separating the components in the fluid into fractions based upon the difference in density of the mixed together components with the use of centrifugal force when the rotor is spinning;

collecting components having i) a first density via a first tube connected to the output port at the first end on the rotor, ii) a second density via a second tube connected to the output port at the second end on the rotor, iii) a third density via a third tube connected to the output port at the junction on the rotor and iv) a fourth density via a fourth tube connected to the output port between the input port and the output port at the first end.

10. The method of claim 9 wherein the components having a first density comprise high density sub-micron particles that have a density greater than the components with a second density, a third density or a fourth density.

11. The method of claim 10 wherein the high density sub-micron particles are functionalized to capture a first component from the components mixed together in the fluid.

12. The method of claim 9 wherein the fluid is blood.

13. The method of claim 12 wherein the components having a first density includes exosomes or oncosomes.

14. The method of claim 12 wherein the components having a second density include plasma.

15. The method of claim 12 wherein components having a third density includes buffy coat with or without circulating tumor cells.

16. The method of claim 12 wherein the components having a fourth density include red blood cells.

17. The method of claim 9 wherein the fluid is supplied to the rotor via the input tube by a pump.

18. The method of claim 9 wherein the components collected from the first tube, the second tube, or the fourth tube are pumped from the rotor to a reservoir.

19. The method of claim 18 wherein the reservoir is an animal or a container.

20. The method of claim 19 wherein the animal is a human.

* * * * *